US010835562B2

(12) United States Patent
Chung

(10) Patent No.: US 10,835,562 B2
(45) Date of Patent: Nov. 17, 2020

(54) COMPOSITION FOR ALCOHOL OR ACETALDEHYDE DEGRADATION COMPRISING PROBIOTICS

(71) Applicant: CELL BIOTECH CO., LTD., Gyeonggi-do (KR)

(72) Inventor: Myung Jun Chung, Seoul (KR)

(73) Assignee: CELL BIOTECH CO., LTD. (KR)

( * ) Notice: Subject to any disclaimer, the term of this patent is extended or adjusted under 35 U.S.C. 154(b) by 62 days.

(21) Appl. No.: 15/976,104

(22) Filed: May 10, 2018

(65) Prior Publication Data
US 2018/0333441 A1 Nov. 22, 2018

(30) Foreign Application Priority Data

May 18, 2017 (KR) ........................ 10-2017-0061853

(51) Int. Cl.
| | |
|---|---|
| A61K 35/747 | (2015.01) |
| A23L 33/135 | (2016.01) |
| A61P 35/00 | (2006.01) |
| A61K 35/745 | (2015.01) |
| A61P 43/00 | (2006.01) |
| A61P 1/16 | (2006.01) |
| A61P 25/32 | (2006.01) |
| A61K 36/484 | (2006.01) |
| C12N 1/20 | (2006.01) |
| A61K 36/28 | (2006.01) |
| A61K 35/744 | (2015.01) |

(52) U.S. Cl.
CPC .......... *A61K 35/747* (2013.01); *A23L 33/135* (2016.08); *A61K 35/744* (2013.01); *A61K 35/745* (2013.01); *A61K 36/28* (2013.01); *A61P 1/16* (2018.01); *A61P 25/32* (2018.01); *A61P 35/00* (2018.01); *A61P 43/00* (2018.01); *C12N 1/20* (2013.01)

(58) Field of Classification Search
CPC .. A61K 35/747; A61K 35/744; A61K 35/745; A61K 36/28; A61K 36/484; A23L 33/135; A61P 43/00; A61P 1/16; A61P 25/32; A61P 35/00; A61P 35/744; C12N 1/20
USPC ...................................................... 424/93.45
See application file for complete search history.

(56) References Cited

U.S. PATENT DOCUMENTS

| | | | |
|---|---|---|---|
| 2006/0233774 A1 | 10/2006 | Lim et al. | |
| 2010/0278975 A1* | 11/2010 | Chung ................. | A61K 35/747 426/61 |
| 2012/0282304 A1* | 11/2012 | Chung ................. | A61K 35/744 424/400 |
| 2014/0335187 A1 | 11/2014 | Carpenter | |
| 2014/0363501 A1 | 12/2014 | Chen et al. | |

FOREIGN PATENT DOCUMENTS

| | | | |
|---|---|---|---|
| CN | 104068393 | * | 10/2014 |
| EP | 2251019 | | 11/2010 |
| JP | 2001-226277 | | 8/2001 |
| JP | 2005-41853 | | 2/2005 |
| KR | 10-2006-0059588 | | 6/2006 |
| KR | 10-2006-0065753 | | 6/2006 |
| KR | 10-0609779 | | 8/2006 |
| KR | 10-2016-0013069 | | 2/2016 |
| KR | 10-2016-0059137 | | 5/2016 |
| WO | WO 2015/017625 | * | 5/2015 |
| WO | WO 2015/095241 | * | 6/2015 |
| WO | WO 2017/037058 | | 3/2017 |

OTHER PUBLICATIONS

Wikipedia, Human gastrointestinal microbiota, Accessed Nov. 24, 2019, Available online at: en.wikipedia.org/wiki/Human_gastrointestinal_microbiota.*
MicrobeWiki, Pediococcus pentosaceus, Accessed Nov. 24, 2019, Available online at: microbewiki.kenyon.edu/index.php/Pediococcus_pentosaceus.*
Database WPI Week 201645 Thomson Scientific, London, GB; AN 2016-30967X XP002785682, & KR 2016 0053447 A (Cell Biotech Co Ltd) May 13, 2016 (abstract).
Database WPI Week 201833 Thomson Scientific, London, GB; AN 2018-36036D XP002785683, & KR 101 853603 B1 (Cell Biotech Co Ltd) May 2, 2018 (abstract).
Database WPI Week 200682 Thomson Scientific, London, GB; AN 2006-810149 XP002785684, & KR 2006 0059588 A (Korea Yakult Co Ltd) Jun. 2, 2006 (abstract).
Database WPI Week 201533 Thomson Scientific, London, GB; AN 2015-281246 XP002785685, & CN 104 415 062 A (Univ Hungkuang) Mar. 18, 2015 (abstract).
Database WPI Week 201460 Thomson Scientific, London, GB; AN 2014-R18692 XP002785686, & CN 103 893 215 A (Univ Yangzhou) Jul. 2, 2014 (abstract).
Database WPI Week 201468 Thomson Scientific, London, GB; AN 2014-S66749 XP002785687, & CN 103 937 716 A (Univ Yangzhou) Jul. 23, 2014 (abstract).
Database WPI Week 201839 Thomson Scientific, London, GB; AN 2018-230023 XP002785688, & CN 107 789 370 A (Univ Wenzhou Medical First Affiliated) Mar. 13, 2018 (abstract).

(Continued)

*Primary Examiner* — Jennifer M.H. Tichy
(74) *Attorney, Agent, or Firm* — Sheridan Ross P.C.

(57) ABSTRACT

The present invention relates to a composition for alcohol or acetaldehyde degradation, which comprises probiotics. The composition of the present invention has a significant synergistic effect on the degradation of alcohol or acetaldehyde, when the probiotics are administered alone or in combination or the composition further comprises excipients. In addition, the composition according to the present invention may effectively degrade alcohol and acetaldehyde, thereby not only treating or preventing alcohol-induced diseases, but also effectively relieving hangovers caused by excessive drinking.

1 Claim, 8 Drawing Sheets

(56) References Cited

OTHER PUBLICATIONS

Database WPI Week 200682 Thomson Scientific, London, GB; AN 2006-810267 XP002785844, & KR 2006 0065753 A (Maeil Dairy Ind Co Ltd) Jun. 14, 2006 (abstract).
Ball et al. "A Review of Silybum marianum (Milk Thistle) as a Treatment for Alcoholic Liver Disease," Journal of Clinical Gastroenterol, Jul. 2005, vol. 39, No. 6, pp. 520-528.
Gratz et al. "Probiotics and gut health: A special focus on liver diseases," World Journal of Gastroenterology, Jan. 2010, vol. 16, No. 4, pp. 403-410.
Nanji et al. "Lactobacillus Feeding Reduces Endotoxemia and Severity of Experimental Alcoholic Liver (Disease)," Proceedings of the Society for Experimental Biology and Medicine, Sage Publications LTD, GB, Jan. 1994, vol. 205, No. 3, pp. 243-247.
Extended Search Report for European Patent Application No. 18172925.2, dated Nov. 20, 2018, 13 pages.
Official Action for Japan Patent Application No. 2018-095818, dated Apr. 12, 2019, 9 pages.

\* cited by examiner

COMPOSITION FOR ALCOHOL OR ACETALDEHYDE DEGRADATION COMPRISING PROBIOTICS

CROSS-REFERENCE TO RELATED APPLICATION

This application claims priority to Korean Patent Application No. 10-2017-0061853, filed on May 18, 2017, the disclosure of which is incorporated herein by reference in its entirety.

BACKGROUND OF THE INVENTION

Field of the Invention

The present invention relates to a composition for alcohol or acetaldehyde degradation, which comprises probiotics.

Description of the Related Art

The liver is a very important organ that controls overall energy metabolism in the human body, functions to store various metabolites and synthetic products, including bilirubin, bile acid, cholesterol, phospholipids and the like, or distribute them to the whole body, and neutralizes toxins or plays a role as a major immune organ.

Regarding deaths caused by diseases in Korea, the number of deaths caused by liver diseases is 22.9 per 100,000, which ranks the fourth leading cause of death, and liver diseases caused by alcohol consumption occupy a high proportion of liver diseases.

According to a survey conducted by the World Health Organization on alcohol consumption in 153 countries, alcohol consumption per adult in Korea is 14.4 L per year, which ranks the second in the world, and about 23,000 people die each year from accidents and diseases caused by drinking alcohol, resulting in an economic loss of 16 trillion won (Korean currency).

Since the alcohol cannot be stored in the body and should be discharged out of the body, alcohol metabolism in the liver is very important. The alcohol metabolism process comprises: stage 1 in which ethanol is oxidized into acetaldehyde by alcohol dehydrogenase, catalase and microsomal ethanol-oxidizing system enzyme; stage 2 in which acetaldehyde is oxidized into acetic acid by aldehyde dehydrogenase; and stage 3 in which acetic acid is degraded into water and carbon dioxide, which are finally discharged from the lungs.

About 20% of the alcohol is absorbed in the stomach and the remainder is mostly absorbed in the small intestine. About 90% of the alcohol absorbed undergoes metabolism in the liver. Acetaldehyde generated in stage 1 as described above may cause damage to liver cells by its toxicity, resulting in acute/chronic alcoholic liver diseases. The alcoholic liver diseases are largely classified into alcoholic fatty liver, alcoholic hepatitis, and alcoholic liver cirrhosis. Liver injury mechanisms include mechanisms caused by alcohol itself, mechanisms caused by metabolites such as acetaldehyde, mechanisms caused by immune responses, and the like. Particularly, acetaldehyde causes lipid peroxidation, binds to the cytoplasm, disrupts the mitochondrial electron transport system, interferes with the function of microtubles, forms protein adducts, and increases collagen synthesis, indicating that it can act as a major cause of hepatotoxicity.

In addition, alcohol metabolism can result in the generation of a number of fatty acids, and fatty accumulation in the liver can cause alcoholic fatty liver. When the alcoholic fatty liver progresses to chronic liver diseases, alcoholic hepatitis can lead to cirrhosis.

Thus, the alcohol metabolism mostly occurs in the liver. For this reason, when alcohol can be treated in the small and large intestines in order to ease burden on the liver, the incidence of the diseases as described above can be lowered.

Meanwhile, in recent years, probiotics have been extensively applied for the prevention and treatment of diseases. In particular, it is known that probiotics have the effect of inhibiting the proliferation and putrefactive activity of intestinal putrefactive bacteria and pathogenic bacteria (Schrezenmeir J, De Vrese M: Am J Clin Nutr. 73(2001), P 361S-4S). In addition, it has been reported that probiotics can exhibit the effect of inhibiting the proliferation of harmful bacteria that produce ammonia, amine or the like, thereby suppressing the production of toxic substances and reducing blood ammonia and alpha-amino acid nitrogen concentrations, thereby alleviating the symptoms of liver diseases. However, up to now, studies on probiotics capable of effectively degrading alcohol and/or acetaldehyde have been limited.

SUMMARY OF THE INVENTION

It is an object of the present invention to provide a composition for alcohol degradation, which comprises probiotics according to the present invention.

Another object of the present invention is to provide a composition for acetaldehyde degradation, which comprises probiotics according to the present invention.

Still another object of the present invention is to provide a food composition for alcohol degradation, which comprises probiotics according to the present invention.

Still another object of the present invention is to provide a food composition for relieving hangovers, which comprises probiotics according to the present invention.

Yet another object of the present invention is to provide a pharmaceutical composition for the prevention or treatment of alcohol-induced diseases, which comprises probiotics according to the present invention.

However, objects which are to be achieved by the present invention are not limited to the above-mentioned objects, and other objects of the present invention will be clearly understood by those skilled in the art from the following description.

The present inventors have found that when alcohol or acetaldehyde is added to probiotics according to the present invention, the alcohol and/or acetaldehyde is effectively degraded, and when a composition comprising the probiotics further comprises licorice and milk thistle extracts, a significant synergistic effect on the degradation is obtained, thereby completing the present invention.

According to one embodiment of the present invention, there is provided a composition for alcohol degradation, which comprises at least one probiotic strain selected from the group consisting of *Lactobacillus* spp., *Bifidobacterium* spp., *Streptococcus* spp., and *Enterococcus* spp.

As used herein, "probiotics" may be defined as living microbial food supplements which beneficially affect the host by improving the intestinal microbial balance, or more broadly, as living microorganisms which upon ingestion in certain numbers exert health effects beyond inherent basic nutrition. These probiotics should not only survive in the conditions of manufacturing, processing, packaging and storage, but then also must survive passage through the gastrointestinal tract, so that probiotic remains viable to provide a positive healing effect.

In the present invention, the probiotic lactic acid bacteria strains may be grown by general culture processes for lactic acid bacteria, and recovered by a separation process such as centrifugation, and prepared as probiotics by, but not limited to, freeze drying, before use.

As used herein, the term "alcohol degradation" means an alcohol metabolism process in which alcohol absorbed in the body is degraded in the liver. Specifically, the term means a process comprising: stage 1 in which ethanol is oxidized into acetaldehyde by alcohol dehydrogenase, catalase and microsomal ethanol-oxidizing system enzyme; stage 2 in which acetaldehyde is oxidized into acetic acid by aldehyde dehydrogenase; and stage 3 in which acetic acid is degraded into water and carbon dioxide. For the purpose of the present invention, the alcohol degradation may be one in which stage 1 or stage 2 is performed by probiotics.

In the present invention, the *Lactobacillus* spp. may be at least one strain selected from the group consisting of *Lactobacillus acidophilus, Lactobacillus rhamnosus, Lactobacillus plantarum, Lactobacillus casei, Lactobacillus paracasei, Lactobacillus reuteri, Lactobacillus fermentum, Lactobacillus helveticus, Lactobacillus gasseri,* and *Lactobacillus lactis*. Preferably, it may be *Lactobacillus casei* or *Lactobacillus gasseri*. More preferably, the *Lactobacillus casei* may be *Lactobacillus casei* CBT LC5 (accession number: KCTC 12398BP), and the *Lactobacillus gasseri* may be *Lactobacillus gasseri* CBT LGA1 (accession number: KCTC 12936BP), but the scope of the present invention is not limited thereto.

When the composition according to the present invention comprises *Lactobacillus casei* or *Lactobacillus gasseri* as a probiotic strain, it may exhibit the effect of more effectively degrading alcohol and/or acetaldehyde in an initial stage after addition of the alcohol and/or acetaldehyde.

In addition, the *Bifidobacterium* spp. in the present invention may be at least one strain selected from the group consisting of *Bifidobacterium longum, Bifidobacterium lactis, Bifidobacterium infantis, Bifidobacterium breve* and *Bifidobacterium bifidum*. Preferably, it may be *Bifidobacterium lactis* or *Bifidobacterium breve*. More preferably, the *Bifidobacterium lactis* may be *Bifidobacterium lactis* CBT BL3 (accession number: KCTC 11904BP), and the *Bifidobacterium breve* may be *Bifidobacterium breve* CBT BR3 (accession number: KCTC 12201BP), but the scope of the present invention is not limited thereto.

When the composition according to the present invention comprises *Bifidobacterium breve* as a probiotic strain, it may effectively increase the degradation of particularly acetaldehyde.

In addition, the *Enterococcus* spp. in the present invention may be at least one strain selected from among *Enterococcus faecium* and *Enterococcus faecalis*.

In addition, the *Streptococcus* spp. in the present invention may be *Streptococcus thermophiles*.

Preferably, the composition according to the present invention may comprise all *Lactobacillus gasseri, Lactobacillus casei, Bifidobacterium lactis* and *Bifidobacterium breve*, but is not limited thereto. When the composition comprising all the probiotic strains as described above, it has a significant synergistic effect on the degradation of alcohol and acetaldehyde.

The composition for alcohol degradation according to the present invention may further comprise at least one of a licorice extract, a milk thistle extract and *Pediococcus* spp. When the composition further comprises the licorice extract, the *Pediococcus* spp. and/or the milk thistle extract, it may exhibit a synergistic effect of promoting the degradation of alcohol and acetaldehyde.

As used herein, the term "licorice extract" means a light yellow crystal or powder form obtained by extracting the root or stem of licorice and concentrating the extract. It was reported that the licorice extract contains flavonoids which exhibit anticancer effects, have anti-aging and anti-inflammatory effects, and are effective for the prevention or treatment of atopy and the like.

As used herein, the term "milk thistle extract" means an extract of *Silybum marianum*, a plant belonging to the family Asteraceae, which has large thorny leaves and round red-purple flowers. The milk thistle extract contains the antioxidant compound silymarin and the like, and thus may be used as a therapeutic agent or a nutrient against various diseases of liver, kidney, gallbladder and the like.

However, the licorice or milk thistle extract in the present invention may be obtained by a conventional extraction method using an organic solvent such as ethanol, hexane, chloroform, methanol or the like.

Furthermore, the *Pediococcus* spp. in the present invention may be *Pediococcus pentosaceus*.

According to another embodiment of the present invention, there is provided a food composition for alcohol degradation, which comprises at least one probiotic strain selected from the group consisting of *Lactobacillus* spp., *Bifidobacterium* spp., *Streptococcus* spp. and *Enterococcus* spp.

In connection with the food composition according to the present invention, the contents about *Lactobacillus* spp., *Bifidobacterium* spp., *Streptococcus* spp., *Enterococcus* spp. and *Pediococcus* spp., accession numbers, combinations of strains, a licorice extract and a milk thistle extract overlap with those described above with respect to the composition for alcohol degradation, and thus the detailed description thereof will be omitted below.

The food composition according to the present invention may be prepared as various foods, for example, beverages, gums, teas, vitamin complexes, powders, granules, tablets, capsules, confectionery, cakes, bread and the like. When the probiotic strain according to the present invention is contained in the food composition, it may be added in an amount of 0.1 to 50 wt % based on the total weight of the food composition.

When the food composition is prepared as a beverage, there is no particular limitation, except that the beverage contains the food composition at the indicated percentage. The beverage may additionally contain various flavorings or natural carbohydrates, like conventional beverages. Examples of the natural carbohydrates include monosaccharides such as glucose, disaccharides such as fructose, polysaccharides such as sucrose, conventional sugars such as dextrin, cyclodextrin or the like, and sugar alcohols such as xylitol, sorbitol, erythritol or the like. Examples of the flavorings include natural flavorings (thaumatin, *stevia* extracts, such as rebaudioside A, glycyrrhizin, etc.) and synthetic flavorings (saccharin, aspartame, etc.).

In addition, the food composition of the present invention may contain various nutrients, vitamins, minerals (electrolytes), flavorings such as synthetic flavorings and natural flavorings, colorants, pectic acid and its salt, alginic acid and its salt, organic acids, protective colloidal thickeners, pH adjusting agents, stabilizers, preservatives, glycerin, alcohol, carbonizing agents which are used in carbonated beverages, etc.

These components may be used individually or in combination. Although the proportion of these additives is not critical to the present invention, it is generally selected in the range of 0.1 to about 50 parts by weight based on 100 parts by weight of the food composition of the present invention.

In addition, the food composition of the present invention may be administered orally as a food or nutritional product, such as a milk or whey based fermented dairy product, or as a food supplement or a functional health food. Specifically, examples of the product include, but are not limited to, an edible product, such as a dairy product, drink, juice, soup or children's food. The "dairy product" means any liquid or semi-solid milk or whey based product having a varying fat content. The dairy product may be, for example, cow's milk, goat's milk, sheep's milk, cream, full-fat milk, whole milk, low-fat milk or skim milk, ultrafiltered milk, diafiltered milk, microfiltered milk, or recombined milk from powdered milk or whey through any processing, or a processed product, such as yoghurt, curdled milk, curd, sour milk, sour whole milk, butter milk, other fermented milk products, such as viili, filling of snack bars, etc. Another important group includes milk beverages, such as whey beverages, fermented milks, condensed milks, infant or baby milks; ice cream; milk-containing food such as sweets.

According to still another embodiment of the present invention, there is provided a food composition for relieving hangovers, which comprises at least one probiotic strain selected from the group consisting of *Lactobacillus* spp., *Bifidobacterium* spp., *Streptococcus* spp. and *Enterococcus* spp.

In connection with the functional health food for relieving hangovers according to the present invention, the contents about Probiotis, *Lactobacillus* spp., *Bifidobacterium* spp., *Pediococcus* spp., *Streptococcus* spp., *Enterococcus* spp., accession numbers, combinations of strains, a licorice extract, a milk thistle extract and a food composition overlap with those described above with respect to the composition for alcohol degradation, and thus the detailed description thereof will be omitted below.

As used herein, "relieving hangovers" is defined as follows. It was reported that a change in the activity of aldehyde dehydrogenase in the liver has an important effect on the detoxification and metabolism of reactive aldehyde. In this procedure, alcohol and aldehyde cause damage to liver cells and brain cells and causes hangovers that cause vomiting and headache and also cause chills or abdominal pain in severe cases. In addition, for persons who produce insufficient aldehyde dehydrogenase, alcohol and aldehyde put more burden on liver and interfere with normal metabolism, resulting in more severe hangovers. Particularly, aldehyde dehydrogenases include type II aldehyde dehydrogenase that initiates degradation even when acetaldehyde is present at low concentrations, and type I aldehyde dehydrogenase that does not act unless acetaldehyde is present at high concentrations. In Asians, acetaldehyde degradation is generally slow due to deficiency or lack of type II aldehyde dehydrogenase, and thus the above-described harmful actions of non-degraded acetaldehyde and ethanol can interfere with normal metabolism, resulting in various hangovers.

Accordingly, "relieving hangovers" as used herein means eliminating hangovers caused by alcohol consumption and reducing blood alcohol concentrations. For the purpose of the present invention, relieving hangovers may be induced by intestinal degradation of alcohol absorbed with the probiotic strain according to the present invention before the alcohol enters the liver, but is not limited thereto.

According to still another embodiment of the present invention, there is provided a pharmaceutical composition for prevention or treatment of alcohol-induced disease, which comprises at least one probiotic strain selected from the group consisting of *Lactobacillus* spp., *Bifidobacterium* spp., *Streptococcus* spp. and *Enterococcus* spp.

In connection with the pharmaceutical composition according to the present invention, the contents about *Lactobacillus* spp., *Bifidobacterium* spp., *Streptococcus* spp., *Enterococcus* spp. and *Pediococcus* spp., accession numbers, combinations of strains, a licorice extract and a milk thistle extract overlap with those described above with respect to the composition for alcohol degradation, and thus the detailed description thereof will be omitted below.

As used herein, the term "alcohol-induced disease" means diseases that can occur in the human body due to alcohol consumption. The alcohol-induced diseases may be at least one disease selected from the group consisting of neuropathic diseases, liver diseases, and cancer. However, without being limited thereto, the alcohol-induced diseases may include all diseases that can occur due to cell death caused by acetaldehyde which is a highly toxic metabolite.

However, the neuropathic diseases in the present invention are diseases that can be caused by acetaldehyde-induced damage to cells, particularly brain cells, and examples thereof include, but are not limited to, peripheral nerve polyneuropathy, Alzheimer's disease and the like.

In addition, the liver diseases in the present invention are diseases that can be caused by acetaldehyde-induced damage to cells, particularly liver cells. The liver diseases may be one or more diseases selected from the group consisting of alcoholic fatty liver, alcoholic hepatitis, and liver cirrhosis, but are not limited thereto.

In addition, the cancer in the present invention may be one or more cancers selected from the group consisting of pancreatic cancer, esophagus cancer, oral pharyngeal cancer, liver cancer, colorectal cancer, lung cancer and breast cancer. Preferably, the cancer may be breast cancer with mammary gland in which the toxic metabolite acetaldehyde is likely to accumulate, but the scope of the present invention is not limited thereto.

In the present invention, the pharmaceutical composition may be provided in the form of capsules, tablets, granules, injectable solutions, ointments, powders or drinks, and may be administered to humans.

For use, the pharmaceutical composition according to the present invention may be formulated as oral dosage forms, including powders, granules, capsules, tablets, aqueous suspensions and the like, external preparations, suppositories or sterile injectable solutions, according to conventional methods, but is not limited thereto. The pharmaceutical composition of the present invention may contain a pharmaceutically acceptable carrier. Pharmaceutically acceptable carriers that may be used in the present invention include binders, lubricants, disintegrants, excipients, solubilizers, dispersing agents, stabilizers, suspending agents, pigments, fragrances and the like, which may be used for oral administration; buffers, preservatives, pain-relieving agents, solubilizers, isotonic agents, stabilizers and the like, which may be used as mixtures for injection; and bases, excipients, lubricants, preservatives and the like, which may be used for local administration. The pharmaceutical composition of the present invention may be formulated in various forms by mixing it with the pharmaceutically acceptable carrier as described above. For example, for oral administration, the pharmaceutical composition of the present invention may be formulated as tablets, troches, capsules, elixirs, suspensions, syrups, wafers or the like, and for injection, may be formulated as unit dose ampoules or multi-dose vials. In addition, the pharmaceutical composition of the present invention may be formulated as solutions, suspensions, tablets, capsules, sustained-release preparations, or the like.

Meanwhile, examples of carriers, excipients and diluents suitable for formulation include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil and the like. In addition, the pharmaceutical composition of the present invention may further contain a filler, an anticoagulant, a lubricant, a wetting agent, a fragrance, an emulsifier, a preservative or the like.

The routes of administration of the pharmaceutical composition according to the present invention include, but are not limited to, oral, intravenous, intramuscular, intra-arterial, intra-marrow, intrathecal, intracardiac, transdermal, subcutaneous, intraperitoneal, intranasal, intestinal, local, sublingual or intrarectal routes. Oral or parenteral administration is preferred.

As used herein, the term "parenteral" is meant to include subcutaneous, transdermal, intravenous, intramuscular, intra-articular, intra-synovial, intrasternal, intradural, intra-lesional and intra-cranial injection or infusion techniques. The pharmaceutical composition of the present invention may also be formulated as suppositories for intrarectal administration.

The pharmaceutical composition of the present invention may vary depending on various factors, including the activity of specific compounds used, the patient's age, body weight, general health, sex, diet, the period of administration, the route of administration, excretion rate, the drug content, and the severity of a specific disease to be prevented or treated. The dose of the pharmaceutical composition may be suitably selected by a person skilled in the art depending on the patient's condition, body weight, the severity of the disease, the form of drug, and the route and period of administration, and may be 0.0001 to 50 mg/kg/day or 0.001 to 50 mg/kg/day. The pharmaceutical composition may be administered once or several times a day. The dose is not intended to limit the scope of the present invention in any way. The pharmaceutical composition according to the present invention may be formulated as pills, sugar-coated tablets, capsules, liquids, gels, syrups, slurries, or suspensions.

DESCRIPTION OF SPECIFIC EMBODIMENTS

Figure 1:
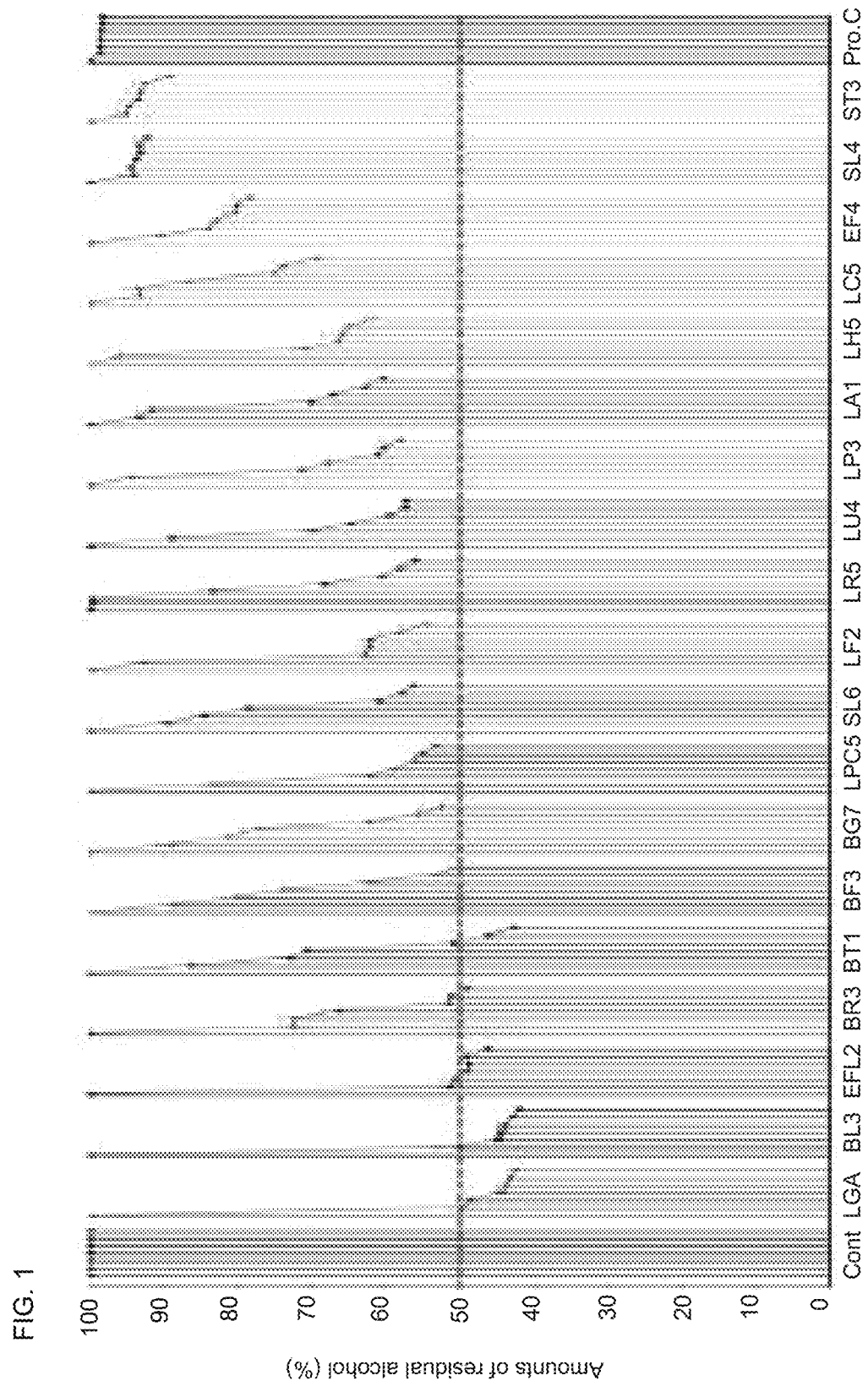
FIG. 1 graphically shows the degree of alcohol degradation measured in an example of the present invention. Each grouping shows percentages determined at time points of 0 hour, 1 hour, 2 hours, 3 hours, 4 hours, 5 hours or 6 hours for each probiotic as described in Example 1. Control (Cont.), *Lactobacillus gasseri* (LGA), *Bifidobacterium lactis* (BL3), *Enterococcus faecalis* (EFL2), *Bifidobacterium breve* (BR3), *Bifidobacterium infantis* (BT1), *Bifidobacterium bifidum* (BF3), *Bifidobacterium longum* (BG7), *Lactobacillus paracasei* (LPC5), *Lactobacillus lactis* (SL6), *Lactobacillus fermentum* (LF2), *Lactobacillus rhamnosus* (LR5), *Lactobacillus reuteri* (LU4), *Lactobacillus plantarum* (LP3), *Lactobacillus acidophilus* (LA1), *Lactobacillus helveticus* (LH5), *Lactobacillus casei* (LC5), *Enterococcus faecium* (EF4), *Pediococcus pentosaceus* (SL4 and also referred to as PP1), *Streptococcus thermophiles* (ST3), Product C (Pro.C).

Hereinafter, the present invention will be described in further detail with reference to examples. It will be obvious to those skilled in the art that these examples are for illustrative purposes only and are not intended to the scope of the present invention.

EXAMPLES

Preparation Example 1: Culturing of Probiotics

In order to examine the ability of probiotics according to the present invention to promote the degradation of alcohol and acetaldehyde, 19 probiotics were cultured. The cultured probiotics were as follows: *Lactobacillus* spp., including

*Lactobacillus acidophilus* (LA1), *Lactobacillus rhamnosus* (LR5), *Lactobacillus plantarum* (LP3), *Lactobacillus casei* (LC5), *Lactobacillus paracasei* (LPC5), *Lactobacillus reuteri* (LU4), *Lactobacillus fermentum* (LF2), *Lactobacillus helveticus* (LH5), *Lactobacillus gasseri* (LGA) and *Lactobacillus lactis* (SL6); *Bifidobacterium* spp., including *Bifidobacterium longum* (BG7), *Bifidobacterium lactis* (BL3), *Bifidobacterium infantis* (BT1), *Bifidobacterium breve* (BR3) and *Bifidobacterium bifidum* (BF3); *Pediococcus* spp., including *Pediococcus pentosaceus* (PP1); *Enterococcus* spp., including *Enterococcus faecium* (EF4) and *Enterococcus faecalis* (EFL2); and *Streptococcus* spp., including *Streptococcus thermophiles* (ST3). After completion of the culturing, the cultures containing the probiotics were centrifuged, and then pellets containing $1\times10^9$ CFU probiotics were collected. The pellets were washed three times with 100 mM potassium phosphate buffer (pH 7.4) to remove impurities, and then were used in the following examples.

Example 1: Effect on Alcohol Degradation

Whether the probiotics according to the present invention have the effect of promoting alcohol degradation was examined.

In order to examine the effect of promoting alcohol degradation, 50 μl of alcohol was added to 450 μl of buffer to a final concentration of 250 mM (about 1.5% alcohol). Next, the pellets obtained in Preparation Example 1 above, a hangover relief drink (manufactured by other company) for promoting alcohol degradation, which was used as a positive control, and a PBS buffer (pH 7.4) for buffering action, were added to the alcohol solution, and each of the solutions was incubated at 37° C. for 1 to 6 hours. Here, the hangover relief drink used was commercially available Condition® (Product C) having a *Hovenia dulcis* extract concentration of 1% as indicated thereon. At each time point, each incubated solution was centrifuged at 5000 rpm at 4° C. for 5 minutes, and the content of alcohol in the supernatant was measured using an ethanol assay kit (Megazyme), and then compared with that in a negative control to which PBS was added, thereby determining the residual alcohol content as a percentage relative to that in the negative control. The results are shown in FIG. 1 and Table 1 below.

TABLE 1

| | Residual alcohol (%) | | | | | |
|---|---|---|---|---|---|---|
| Probiotics | 1 hour | 2 hours | 3 hours | 4 hours | 5 hours | 6 hours |
| PBS pH 7.4 | 100 | 100 | 100 | 100 | 100 | 100 |
| Pro. C | 98.7 | 98.7 | 98.6 | 98.5 | 98.4 | 98.4 |
| LA1 | 93.2 | 91.6 | 70.1 | 67.2 | 62.8 | 60.3 |
| LR5 | 99.7 | 83.4 | 68.2 | 60.5 | 58.0 | 55.9 |
| LP3 | 94.3 | 71.3 | 67.7 | 61.1 | 60.1 | 57.9 |
| LC5 | 93.1 | 93.5 | 86.6 | 75.0 | 73.7 | 69.2 |
| LPC5 | 83.6 | 62.1 | 58.9 | 56.1 | 55.0 | 53.1 |
| LU4 | 89.0 | 69.9 | 64.6 | 59.3 | 57.3 | 57.1 |
| LF2 | 92.8 | 62.8 | 62.3 | 62.2 | 58.4 | 54.7 |
| LH5 | 96.0 | 70.9 | 66.2 | 65.9 | 64.8 | 61.6 |
| LGA | 49.7 | 48.5 | 44.7 | 44.2 | 43.7 | 42.9 |
| BG7 | 89.0 | 77.2 | 81.5 | 62.3 | 55.4 | 52.4 |
| BL3 | 50.0 | 45.0 | 44.5 | 44.2 | 43.1 | 42.3 |
| BT1 | 86.4 | 72.8 | 70.6 | 50.7 | 46.0 | 43.0 |
| BR3 | 72.6 | 78.1 | 73.8 | 51.4 | 51.2 | 48.9 |
| BF3 | 88.8 | 80.2 | 74.0 | 62.4 | 53.3 | 49.9 |
| ST3 | 95.3 | 94.9 | 93.6 | 93.3 | 92.7 | 89.3 |
| SL6 | 89.5 | 84.5 | 78.6 | 60.9 | 57.8 | 56.2 |
| PP1 | 94.0 | 94.4 | 93.8 | 93.1 | 93.2 | 92.2 |
| EF4 | 90.4 | 84.0 | 82.8 | 80.3 | 80.2 | 78.3 |
| EFL2 | 51.1 | 50.6 | 48.9 | 48.6 | 49.0 | 46.2 |

As can be seen in FIG. 1 and Table 1 above, the concentration of alcohol in the hangover relief beverage (manufactured by other company) did not decrease. However, in the probiotics according to the present invention, it could be seen that alcohol degradation occurred in most of the probiotics, even though there was a difference in the degree and time of degradation of alcohol.

In particular, it could be seen that alcohol degradation in *Lactobacillus gasseri* (LGA) and *Bifidobacterium lactis* (BL3) occurred significantly fast so that the residual alcohol content at 1 hours would be only 50%.

The above-described results suggest that the probiotics according to the present invention have the effect of degrading alcohol.

Example 2: Effect on Acetaldehyde Degradation

Whether the probiotics according to the present invention have the effect of promoting acetaldehyde degradation was examined.

The effects of the probiotics of Preparation Example 1 on acetaldehyde degradation were measured in the same manner as described in Example 1. For the measurement, 50 μl of acetaldehyde in place of alcohol was added to 450 μl of buffer to a final concentration of 50 mM, and then the procedure described in Example 1 above was performed. The results are shown in FIG. 2 and Table 2 below.

TABLE 2

| | Residual acetaldehyde (%) | | | | | |
|---|---|---|---|---|---|---|
| Probiotics | 1 hour | 2 hours | 3 hours | 4 hours | 5 hours | 6 hours |
| PBS pH 7.4 | 100 | 100 | 100 | 100 | 100 | 100 |
| Pro. C | 98.7 | 98.7 | 98.2 | 97.9 | 97.5 | 97.2 |
| LA1 | 86.4 | 82.0 | 77.2 | 76.0 | 69.3 | 65.8 |
| LR5 | 88.9 | 86.5 | 74.8 | 72.3 | 66.6 | 62.6 |
| LP3 | 64.4 | 63.2 | 62.7 | 59.9 | 54.5 | 53.3 |
| LC5 | 37.6 | 9.2 | 1.9 | 0.9 | 0.5 | 0.2 |
| LPC5 | 96.9 | 86.5 | 71.1 | 68.2 | 64.4 | 51.3 |
| LU4 | 89.1 | 79.7 | 69.1 | 68.5 | 65.5 | 61.9 |
| LF2 | 79.6 | 77.0 | 70.6 | 63.6 | 58.3 | 56.3 |
| LH5 | 71.6 | 67.3 | 62.7 | 56.0 | 52.8 | 39.9 |
| LGA | 89.2 | 84.7 | 84.0 | 79.7 | 75.0 | 61.9 |
| BG7 | 83.1 | 70.8 | 65.0 | 50.6 | 42.2 | 35.4 |
| BL3 | 84.6 | 69.7 | 65.4 | 53.2 | 47.0 | 41.0 |
| BT1 | 85.1 | 80.9 | 78.6 | 63.3 | 61.0 | 58.5 |
| BR3 | 74.8 | 66.6 | 65.0 | 47.4 | 44.1 | 37.3 |
| BF3 | 79.6 | 71.0 | 68.7 | 52.0 | 49.8 | 42.5 |
| ST3 | 85.2 | 79.7 | 76.3 | 75.9 | 73.8 | 71.9 |
| SL6 | 94.3 | 90.7 | 78.4 | 77.7 | 76.7 | 73.0 |
| PP1 | 97.9 | 78.6 | 74.8 | 67.6 | 64.6 | 62.3 |
| EF4 | 86.2 | 82.5 | 80.6 | 76.7 | 76.1 | 75.9 |
| EFL2 | 77.3 | 74.3 | 73.6 | 72.8 | 70.8 | 69.0 |

Figure 2:
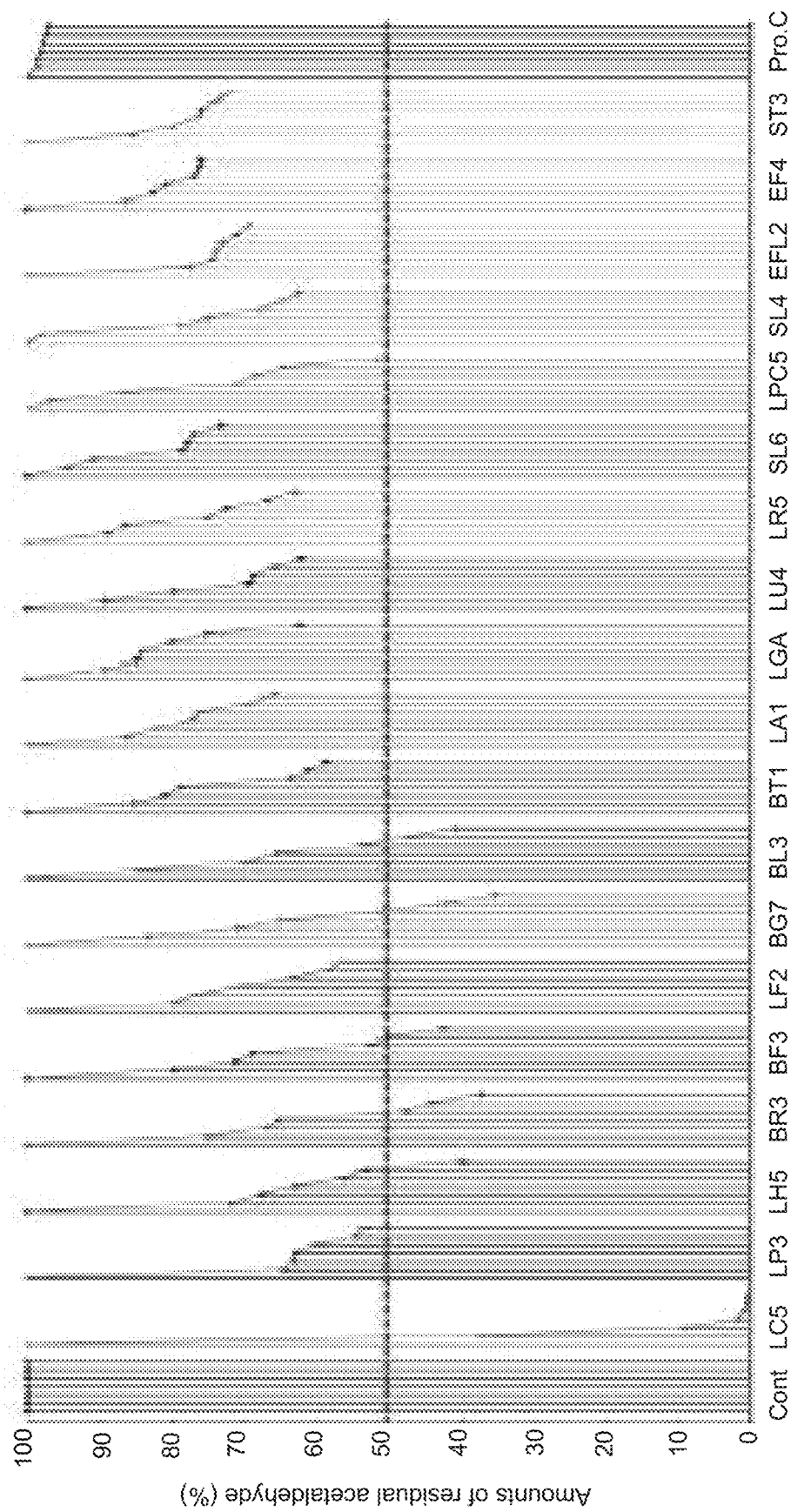
FIG. 2 graphically shows the degree of acetaldehyde degradation measured in an example of the present invention. Each grouping shows percentages determined at time points of 0 hour, 1 hour, 2 hours, 3 hours, 4 hours, 5 hours or 6 hours for each probiotic as described in Example 2. Control (Cont.), *Lactobacillus casei* (LC5), *Lactobacillus plantarum* (LP3), *Lactobacillus helveticus* (LH5), *Bifidobacterium breve* (BR3), *Bifidobacterium bifidum* (BF3), *Lactobacillus fermentum* (LF2), *Bifidobacterium longum* (BG7), *Bifidobacterium lactis* (BL3), *Bifidobacterium infantis* (BT1), *Lactobacillus acidophilus* (LA1), *Lactobacillus gasseri* (LGA), *Lactobacillus reuteri* (LU4), *Lactobacillus rhamnosus* (LR5), *Lactobacillus lactis* (SL6), *Lactobacillus paracasei* (LPC5), *Pediococcus pentosaceus* (SL4 and also referred to as PP1), *Enterococcus faecalis* (EFL2), *Enterococcus faecium* (EF4), *Streptococcus thermophiles* (ST3), Product C (Pro.C).

As can be seen in FIG. 2 and Table 2 above, the concentration of acetaldehyde in the negative control and the hangover relief drink (manufactured by other company) did not decrease. However, in the probiotics according to the present invention, it could be seen that the degradation of acetaldehyde occurred in most of the probiotics, even though there was a difference in the degree and time of degradation of acetaldehyde.

In particular, *Lactobacillus casei* (LC5) and *Bifidobacterium breve* (BR3) showed residual acetaldehyde concentrations of 0.2% and 37.3%, respectively, at 6 hours, indicating that they very effectively degraded acetaldehyde.

Example 3: In Vitro Examination of the Effects of Combinations of Probiotics on Degradation of Alcohol and Acetaldehyde Whether combinations of the probiotics according to the present invention have the effects of degrading alcohol and acetaldehyde was examined.

Figure 3:
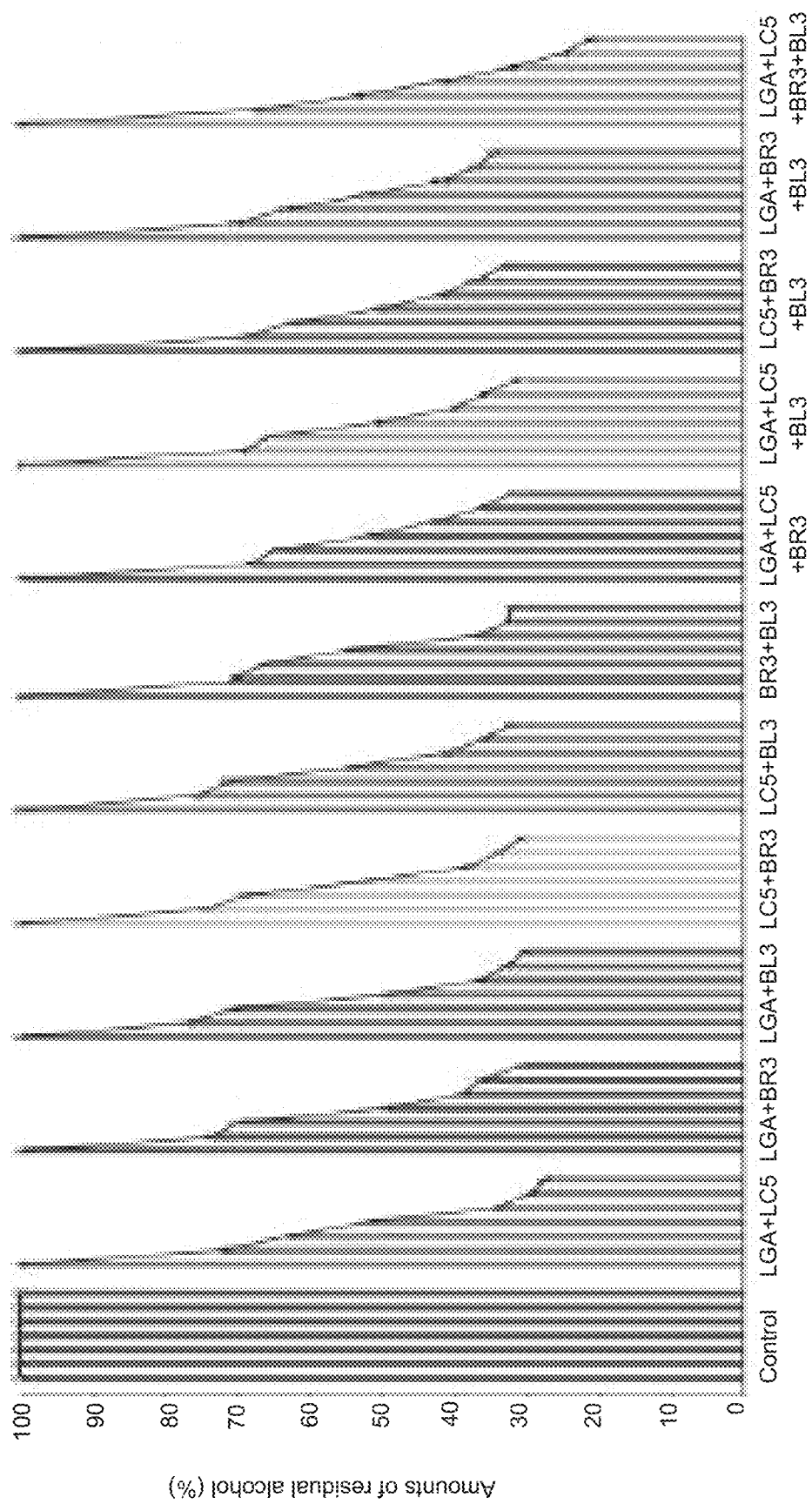
FIG. 3 graphically shows the degree of alcohol degradation measured in an example of the present invention. Each grouping shows percentages determined at time points of 0 hour, 1 hour, 2 hours, 3 hours, 4 hours, 5 hours or 6 hours for each combination of probiotics as described in Example 3.
Figure 4:
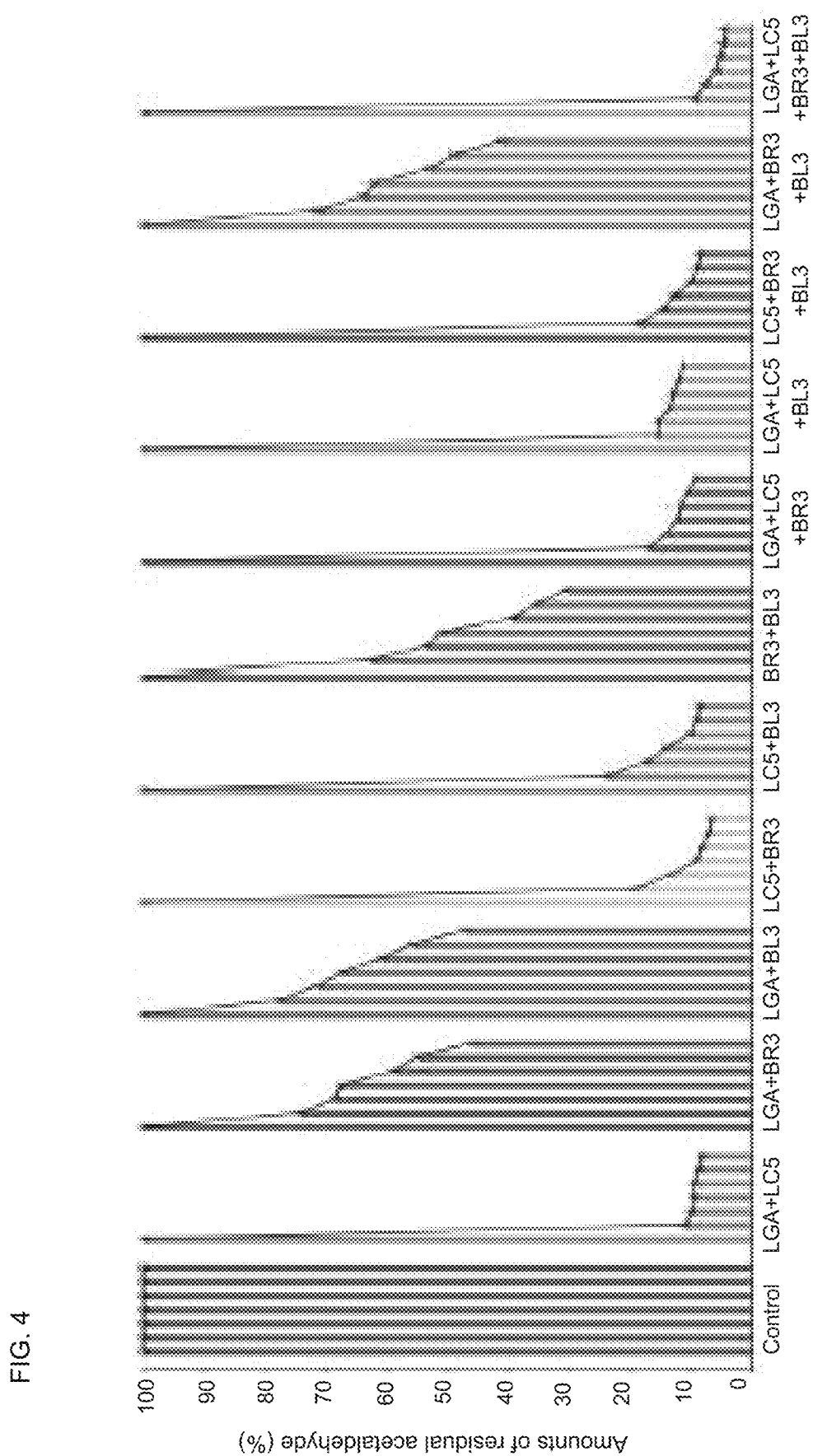
FIG. 4 graphically shows the degree of acetaldehyde degradation measured in an example of the present invention Each grouping shows percentages determined at time points of 0 hour, 1 hour, 2 hours, 3 hours, 4 hours, 5 hours or 6 hours for each combination of probiotics as described in Example 3.

The probiotics were combined as shown in Tables 3 and 4 below, and the residual contents of alcohol and acetaldehyde were measured in the same manner as described in Examples 1 and 2 above. The results of the measurement are shown in FIGS. 3 and 4 and Tables 3 and 4 below.

TABLE 3

| | Residual alcohol (%) | | | | | |
|---|---|---|---|---|---|---|
| Probiotics | 1 hour | 2 hours | 3 hours | 4 hours | 5 hours | 6 hours |
| PBS pH 7.4 | 100 | 100 | 100 | 100 | 100 | 100 |
| LGA + LC5 | 71.9 | 62.6 | 51.3 | 34.4 | 29.4 | 27.6 |
| LGA + BR3 | 73.3 | 69.7 | 49.1 | 39.0 | 36.4 | 30.5 |
| LGA + BL3 | 76.8 | 70.4 | 48.9 | 36.4 | 32.9 | 30.3 |
| LC5 + BR3 | 74.2 | 68.5 | 51.4 | 38.0 | 33.8 | 30.7 |
| LC5 + BL3 | 75.2 | 71.1 | 53.8 | 41.0 | 36.0 | 32.1 |
| BR3 + BL3 | 70.7 | 65.8 | 54.5 | 36.8 | 32.6 | 32.3 |
| LGA + LC5 + BR3 | 68.0 | 64.5 | 51.6 | 42.9 | 36.2 | 32.2 |
| LGA + LC5 + BL3 | 68.6 | 65.6 | 50.1 | 40.2 | 36.0 | 31.5 |
| LC5 + BR3 + BL3 | 69.0 | 62.2 | 50.0 | 41.8 | 37.4 | 33.1 |
| LGA + BR3 + BL3 | 70.0 | 63.0 | 52.0 | 41.6 | 37.2 | 34.4 |
| LGA + LC5 + BR3 + BL3 | 67.1 | 53.2 | 41.8 | 32.2 | 25.1 | 21.2 |

TABLE 4

| | Residual acetaldehyde (%) | | | | | |
|---|---|---|---|---|---|---|
| Probiotics | 1 hour | 2 hours | 3 hours | 4 hours | 5 hours | 6 hours |
| PBS pH 7.4 | 100 | 100 | 100 | 100 | 100 | 100 |
| LGA + LC5 | 11.1 | 10.1 | 9.8 | 9.7 | 9.0 | 8.5 |
| LGA + BR3 | 74.2 | 68.7 | 67.6 | 58.7 | 55.0 | 45.8 |
| LGA + BL3 | 77.9 | 71.6 | 67.5 | 60.8 | 56.0 | 47.1 |
| LC5 + BR3 | 19.4 | 13.2 | 9.3 | 8.2 | 7.2 | 6.8 |
| LC5 + BL3 | 23.7 | 17.4 | 14.1 | 10.3 | 9.3 | 8.8 |
| BR3 + BL3 | 62.5 | 53.4 | 51.1 | 39.3 | 35.5 | 30.5 |
| LGA + LC5 + BR3 | 17.1 | 14.1 | 12.4 | 11.9 | 10.7 | 9.4 |
| LGA + LC5 + BL3 | 15.7 | 15.7 | 13.6 | 13.0 | 12.2 | 11.6 |
| LC5 + BR3 + BL3 | 18.6 | 14.6 | 12.8 | 10.1 | 9.1 | 8.7 |
| LGA + BR3 + BL3 | 71.5 | 64.0 | 62.0 | 52.9 | 48.8 | 41.1 |
| LGA + LC5 + BR3 + BL3 | 9.7 | 7.9 | 6.1 | 5.4 | 5.0 | 4.7 |

As can be seen in FIGS. 3 and 4 and Tables 3 and 4 above, a combination of *Lactobacillus gasseri* (LGA), *Lactobacillus casei* (LC5), *Bifidobacterium breve* (BR3) and *Bifidobacterium lactis* (BL3) showed a residual alcohol content of 21.2% at 6 hours. In addition, the combination of the four probiotics showed a residual acetaldehyde content of 9.7% at 1 hour, which was about 28% to 88% lower than those measured when the probiotics were added alone.

From the above results, it can be seen that most combinations of the probiotics had significant synergistic effects on the degradation of alcohol and acetaldehyde compared to when the probiotics were added alone, even though there was a difference in the degree and time of the degradation. In particular, the initial content of acetaldehyde could be significantly lowered when the probiotics were added in combination compared to when the probiotics were added alone.

Example 4: Examination of the Effect of Combination of Probiotics on Degradation of Alcohol and Acetaldehyde Whether the combination of probiotics of Example 3 above according to the present invention would also be effective in vivo was examined. A combination of *Lactobacillus gasseri* (LGA), *Lactobacillus casei* (LC5), *Bifidobacterium breve* (BR3) and *Bifidobacterium lactis* (BL3) (hereinafter referred to as 'CBT 4 strain'), shown to have a good effect in Example 3 above, was administered to six 6-week-old SD male rats in an amount of $10^7$ CFUs/head, and after 30 minutes, 40% alcohol was administered orally to the rats in an amount of 5 g/kg. As positive controls, hangover relief drinks (manufactured by other companies) were administered in amounts of 0.4 ml/head (Product C) and 37 mg/head (Product S), respectively, and as a negative control, the same volume of PBS (pH 7.4) was administered.

In order to examine the changes in alcohol metabolism in the rats, blood was collected from the jugular vein of each of the test rats at 1 hour and 3 hours and from the major abdominal vein at 5 hours. The collected blood was centrifuged at 3000 rpm for 20 minutes to separate sera. The concentrations of ethanol and acetaldehyde in the obtained sera were measured in the same manner as described in Examples 1 and 2 above. The blood collected at 5 hours was analyzed using a blood analyzer, thereby measuring liver function-related indices. The results of the measurement are shown in FIGS. 5 to 8 and Tables 5 to 7 below.

TABLE 5

| | Blood alcohol (mg/dL) | | |
|---|---|---|---|
| Test group | 1 hr | 3 hrs | 5 hrs |
| PBS pH 7.4 | 9.72 ± 1.71 | 10.21 ± 1.40 | 10.92 ± 1.05 |
| PBS pH 7.4 + ethanol | 282.99 ± 8.60 | 272.34 ± 4.92 | 256.65 ± 4.26 |
| Product C + ethanol | 265.11 ± 16.91 | 251.34 ± 11.46 | 245.99 ± 11.42 |
| Product S + ethanol | 268.77 ± 2.79 | 260.95 ± 3.21 | 248.01 ± 7.17 |
| CBT 4 strains + ethanol | 220.87 ± 5.68 | 188.97 ± 9.40 | 142.78 ± 9.81 |

TABLE 6

| | Blood acetaldehyde (mg/dL) | | |
|---|---|---|---|
| Test group | 1 hr | 3 hrs | 5 hrs |
| PBS pH 7.4 | 0.71 ± 0.29 | 0.71 ± 0.29 | 0.62 ± 0.34 |
| PBS pH 7.4 + ethanol | 14.17 ± 0.98 | 11.94 ± 0.68 | 9.18 ± 0.79 |
| Product C + ethanol | 8.29 ± 0.67 | 5.97 ± 0.44 | 4.99 ± 0.50 |
| Product S + ethanol | 10.16 ± 1.06 | 8.11 ± 1.34 | 5.97 ± 0.53 |
| CBT 4 strains + ethanol | 4.36 ± 0.60 | 3.83 ± 0.44 | 3.65 ± 0.44 |

TABLE 7

| Test group | ALT (UI/L) | AST (UI/L) |
|---|---|---|
| PBS pH 7.4 | 35.57 ± 0.88 | 100.66 ± 2.78 |
| PBS pH 7.4 + ethanol | 61.87 ± 3.39 | 156.50 ± 9.42 |

TABLE 7-continued

| Test group | ALT (UI/L) | AST (UI/L) |
|---|---|---|
| Product C + ethanol | 43.25 ± 0.77 | 136.75 ± 3.10 |
| Product S + ethanol | 49.60 ± 2.24 | 140.10 ± 4.95 |
| CBT 4 strains + ethanol | 34.80 ± 2.21 | 117.32 ± 3.89 |

Figure 5:
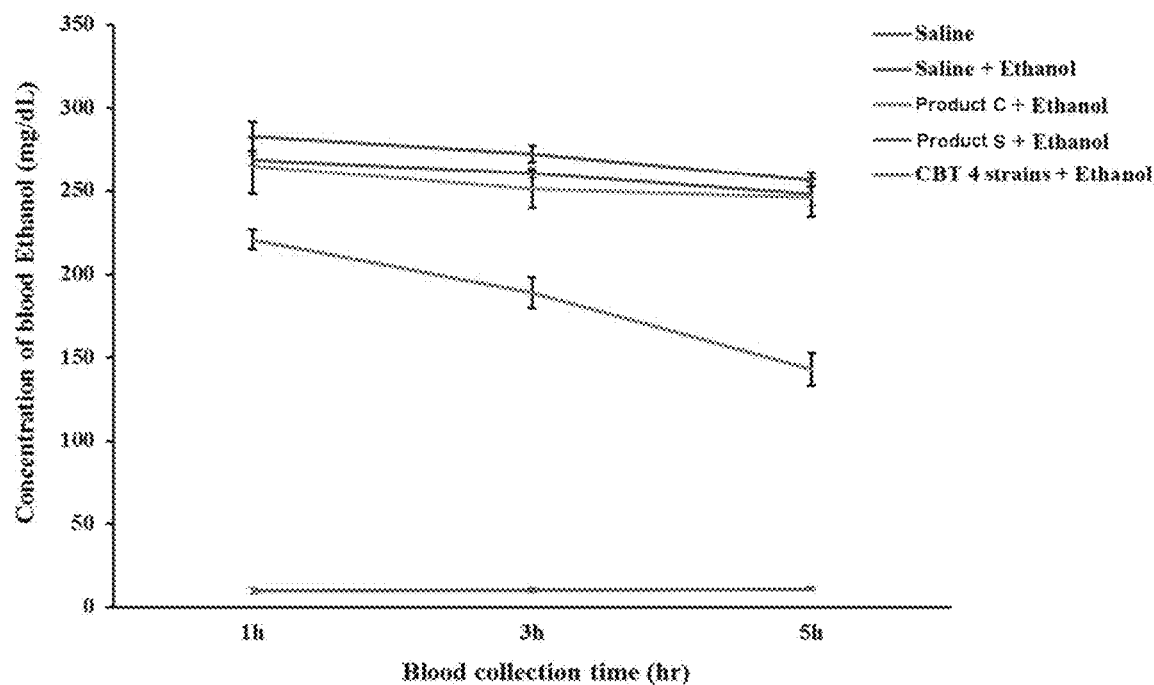
FIG. 5 graphically shows the degree of alcohol degradation by a combination of probiotic strains, measured in an example of the present invention.
Figure 6:
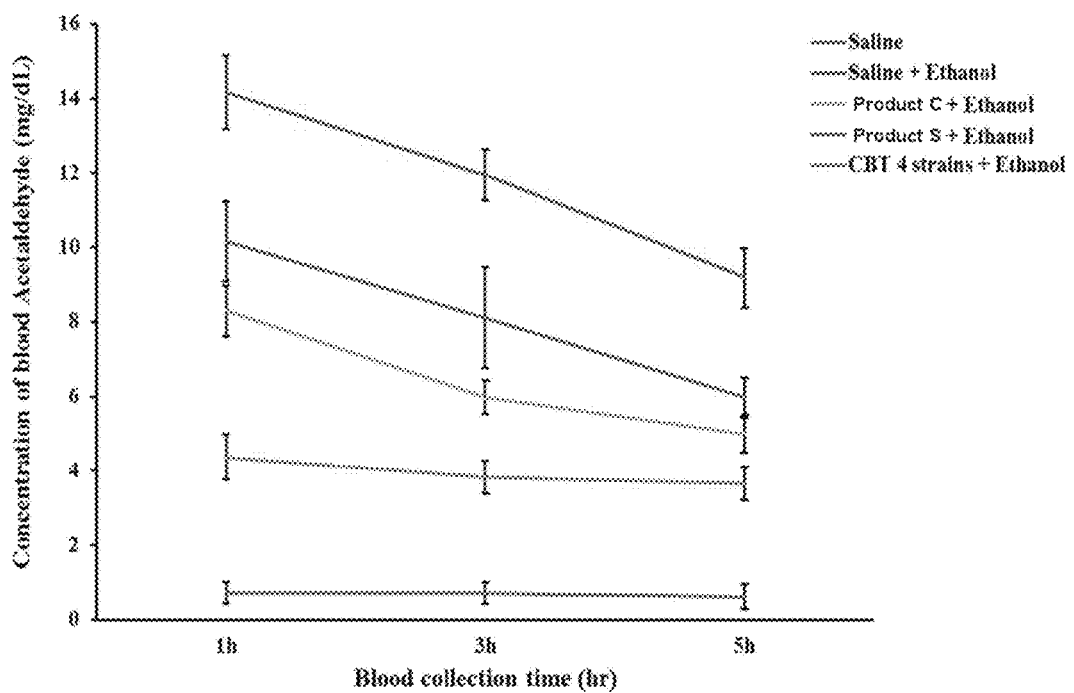
FIG. 6 graphically shows the degree of acetaldehyde degradation by a combination of probiotic strains, measured in an example of the present invention.

As can be seen in FIG. 5 and Table 5 above, like the results of the in vitro experiments, the CBT 4 strain reduced the ethanol content by about 40 and 80 mg/dL compared to the hangover relief products (Product C and Product S manufactured by other companies) at 3 hours and 5 hours. In addition, as can be seen in FIG. 6 and Table 6 above, the CBT 4 strain very significantly reduced the acetaldehyde content to 4.36±0.60 mg/dL at 1 hour.

Figure 7:
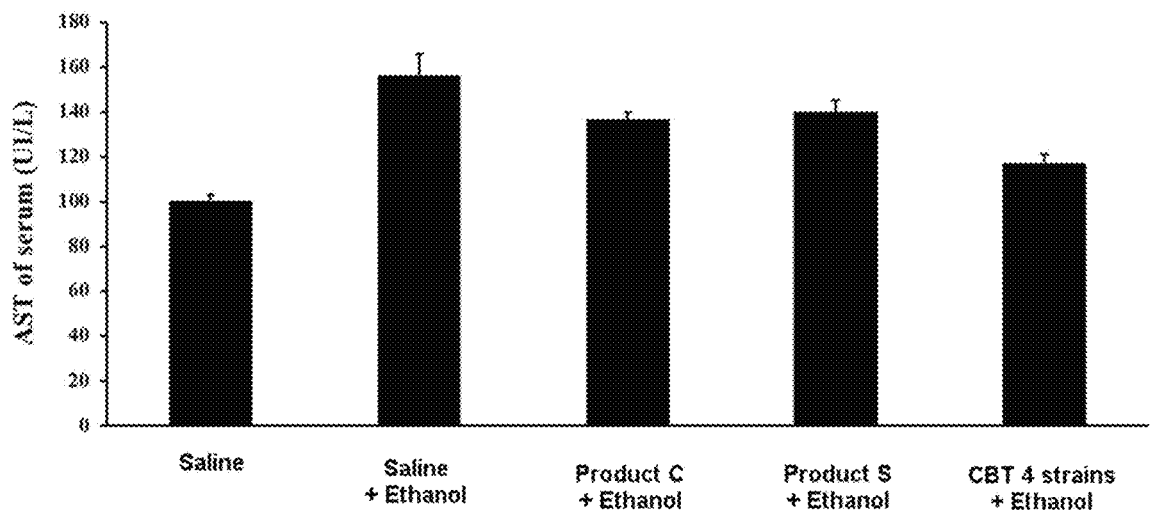
FIG. 7 graphically shows the in vivo liver function-related indices that decreased by a combination of probiotic strains in an example of the present invention.
Figure 8:
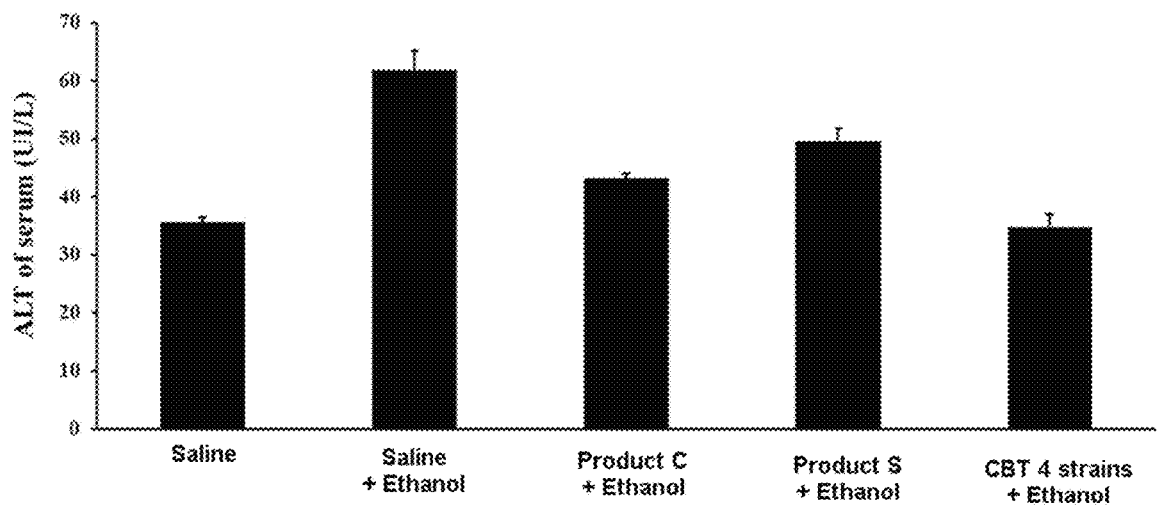
FIG. 8 graphically shows the in vivo liver function-related indices that decreased by a combination of probiotic strains in an example of the present invention.

Furthermore, as can be seen in FIG. 7 and Table 7 above, when the CBT 4 strain was administered, ALT and AST concentrations that were increased by ethanol were lowered to 34.80±2.21 UI/L and 117.32±3.89 UI/L, respectively, which were almost similar to those measured when the negative control PBS was administered.

From the above results, it could be seen that when the probiotics according to the present invention are administered in combination, they have a significant synergistic effect on the degradation of alcohol and acetaldehyde and also very effectively lower the in vivo liver function-related indices compared to the hangover relief products (manufactured by other companies).

Example 5: Effect of Excipients on Degradation of Alcohol and Acetaldehyde

Analysis was performed to determine whether the additional administration of excipients in addition to the combination of probiotics of Example 3 above according to the present invention would have a synergistic effect on the degradation of alcohol and acetaldehyde.

Figure 9:
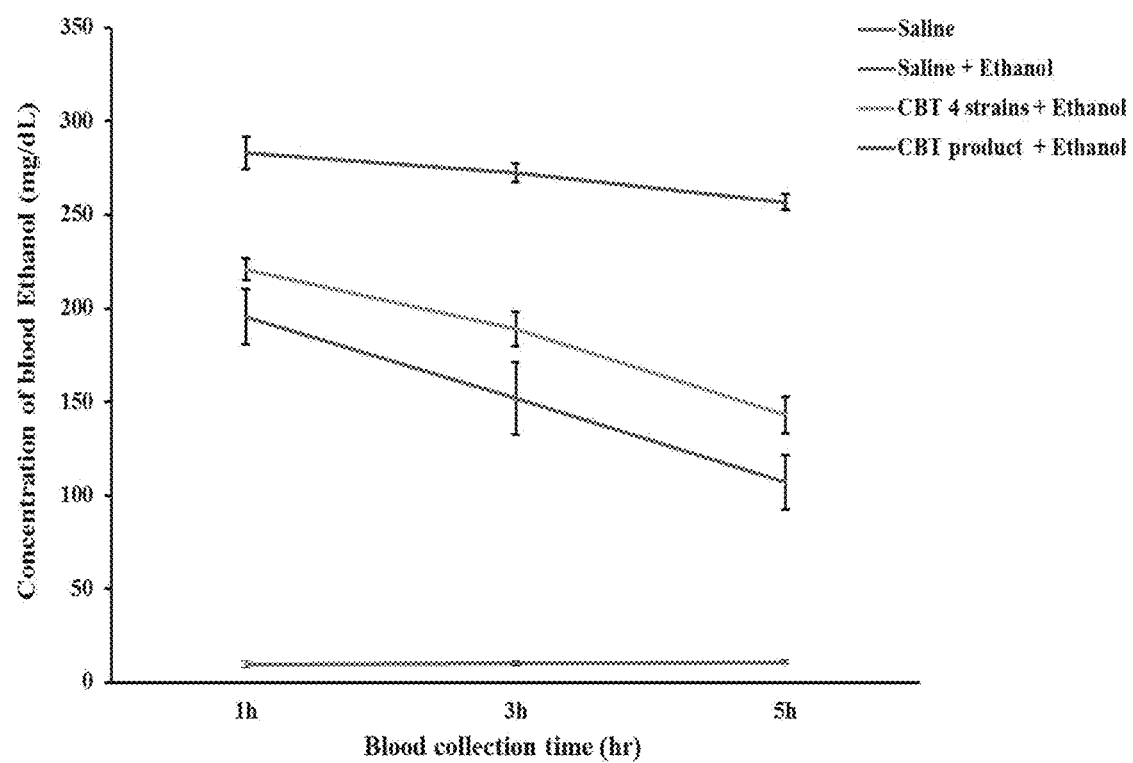
FIG. 9 graphically shows the degree of alcohol degradation by a combination of probiotic strains, measured in an example of the present invention.
Figure 10:
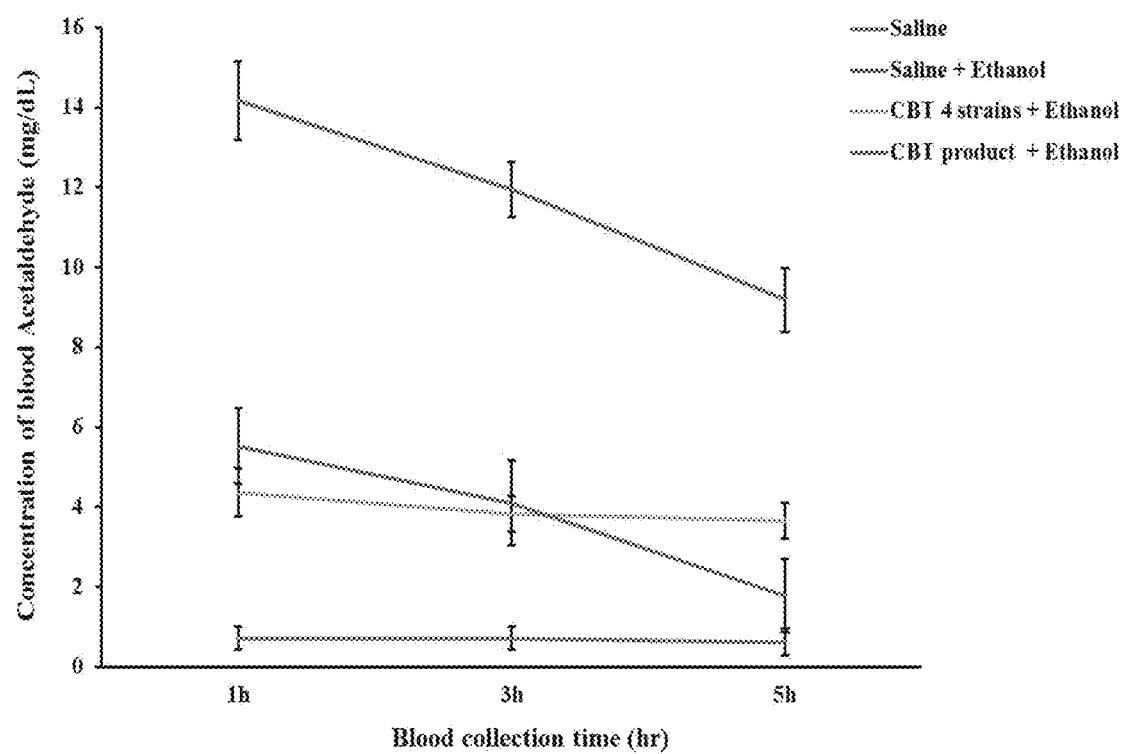
FIG. 10 graphically shows the degree of acetaldehyde degradation by a combination of probiotic strains, measured in an example of the present invention.

Administration was performed as shown in Tables 8 and 9 below. As excipients, a licorice extract, a milk thistle extract and *Pediococcus pentosaceus* (PP1) were additionally administered. Next, residual alcohol and acetaldehyde contents and liver function-related indices were measured in the same manner as described in Example 4 above. The results of the measurement are shown in FIGS. 9 and 10 and Tables 8 and 9 below.

TABLE 8

| | Blood alcohol (mg/dL) | | |
|---|---|---|---|
| Test group | 1 hr | 3 hrs | 5 hrs |
| Saline | 9.72 ± 1.71 | 10.21 ± 1.40 | 10.92 ± 1.05 |
| Saline + ethanol | 282.99 ± 8.60 | 272.34 ± 4.92 | 256.65 ± 4.26 |
| CBT 4 strains + ethanol | 220.87 ± 5.68 | 188.97 ± 9.40 | 142.78 ± 9.81 |
| CBT 4 strains + ethanol + excipients | 195.45 ± 14.69 | 151.97 ± 19.35 | 106.82 ± 14.50 |

TABLE 9

| | Blood acetaldehyde (mg/dL) | | |
|---|---|---|---|
| Test group | 1 hr | 3 hrs | 5 hrs |
| Saline | 0.71 ± 0.29 | 0.71 ± 0.29 | 0.62 ± 0.34 |
| Saline + ethanol | 14.17 ± 0.98 | 11.94 ± 0.68 | 9.18 ± 0.79 |
| CBT 4 strains + ethanol | 4.36 ± 0.60 | 3.83 ± 0.44 | 3.65 ± 0.44 |

TABLE 9-continued

| | Blood acetaldehyde (mg/dL) | | |
|---|---|---|---|
| Test group | 1 hr | 3 hrs | 5 hrs |
| CBT 4 strains + ethanol + excipients | 5.52 ± 0.94 | 4.10 ± 1.06 | 1.78 ± 0.92 |

As can be seen in FIG. 9 and Table 8 above, when the excipients were additionally administered, the blood alcohol concentration was lowered by about 10 to 40 mg/dL compared to when the CBT 4 strains were administered without the excipients. In addition, as can be seen in FIG. 10 and Table 9, when the excipients were additionally administered, the blood acetaldehyde concentration was lowered to 1.78±0.92 mg/dL at 5 hours, which was similar to that measured when the negative control PBS was administered.

From the above-described results, it can be seen that when the combination of probiotics according to the present invention is administered alone or in combination with the excipients, it has a significant synergistic effect on the degradation of alcohol and acetaldehyde compared to the summed degradation effect obtained when these probiotics are administered alone.

As described above, the composition comprising probiotics according to the present invention can exhibit a significant synergistic effect on the degradation of alcohol and/or acetaldehyde, when the probiotics are administered alone or in combination or the composition further comprises excipients.

In addition, the composition according to the present invention can effectively degrade alcohol and acetaldehyde, thereby not only treating or preventing alcohol-induced diseases, but also effectively relieving hangovers caused by excessive drinking.

Although the embodiments of the present invention have been described in detail, it will be obvious to those skilled in the art that the scope of the present invention is not limited to these embodiments and that various changes and modifications are possible without departing from the technical spirit of the present invention as defined in the appended claims.

Accession Numbers

Name of Depositary Institution: Korean Collection for Type Cultures (KCTC) at Korea Research Institute of Bioscience and Biotechnology;

Accession Number: KCTC12936BP;

Date of Deposit: Oct. 22, 2015.

Name of Depositary Institution: Korean Collection for Type Cultures (KCTC) at Korea Research Institute of Bioscience and Biotechnology;

Accession Number: KCTC11904BP;

Date of Deposit: Mar. 30, 2011.

Name of Depositary Institution: Korean Collection for Type Cultures (KCTC) at Korea Research Institute of Bioscience and Biotechnology;

Accession Number: KCTC12201BP;

Date of Deposit: Apr. 27, 2012.

Name of Depositary Institution: Korean Collection for Type Cultures (KCTC) at Korea Research Institute of Bioscience and Biotechnology;

Accession Number: KCTC12398BP;

Date of Deposit: Apr. 5, 2013.

*Lactobacillus gasseri* CBT LGA1 (accession number KCTC12936BP) was deposited on Oct. 22, 2015 with the Korean Collection for Type Cultures (KCTC) at Korea Research Institute of Bioscience and Biotechnology, 125 Gwahak-ro, Yuseong-gu, Daejeon 305-806 PARK, Doo Sang, Director Republic of Korea; *Bifidobacterium animalis* subsp. *Lactis* CBT BL3 (accession number KCTC11904BP) was deposited on Mar. 11, 2011 with the Korean Collection for Type Cultures (KCTC) at Korea Research Institute of Bioscience and Biotechnology, 125 Gwahak-ro, Yuseong-gu, Daejeon 305-806 PARK, Doo Sang, Director Republic of Korea; *Bifidobacterium breve* CBT BR3 (accession number KCTC12201BP) was deposited on Apr. 27, 2012 with the Korean Collection for Type Cultures (KCTC) at Korea Research Institute of Bioscience and Biotechnology, 125 Gwahak-ro, Yuseong-gu, Daejeon 305-806 PARK, Doo Sang, Director Republic of Korea; and *Lactobacillus casei* CBT LC5 was deposited on Apr. 5, 2013 with the Korean Collection for Type Cultures (KCTC) at Korea Research Institute of Bioscience and Biotechnology, 125 Gwahak-ro, Yuseong-gu, Daejeon 305-806 PARK, Doo Sang, Director Republic of Korea. It is averred that the deposited material has been accepted for deposit under the Budapest Treaty on the International Recognition of the Deposit of Microorganisms for the purpose of Patent Procedure and that all restrictions on the availability to the public of the material so deposited will be irrevocably removed upon granting of a patent, and the deposit is intended to meet all of the requirements of 37 C.F.R. 1.801-1.809. The deposits will be maintained in the depository for a period of thirty years, or five years after the last request, or for the enforceable life of the patent, whichever is longer, and will be replaced as necessary during that period.

What is claimed is:

1. A composition for alcohol degradation, comprising at least two probiotic purified strains selected from the group consisting of *Lactobacillus casei*, *Lactobacillus gasseri*, *Bifidobacterium lactis*, and *Bifidobacterium breve*; comprising a licorice extract or a milk thistle extract; and comprising a *Pediococcus pentosaceus*;

wherein the probiotic strain of *Lactobacillus casei* is *Lactobacillus casei* CBT LC5 (accession number: KCTC 12398BP);

wherein the probiotic strain of *Lactobacillus gasseri* is *Lactobacillus gasseri* CBT LGA1 (accession number: KCTC 12936BP);

wherein the probiotic strain of *Bifidobacterium lactis* is *Bifidobacterium lactis* CBT BL3 (accession number: KCTC 11904BP); and wherein the probiotic strain of *Bifidobacterium breve* is *Bifidobacterium breve* CBT BR3 (accession number: KCTC 12201BP).

* * * * *